(12) United States Patent
Hsieh et al.

(10) Patent No.: US 6,421,412 B1
(45) Date of Patent: Jul. 16, 2002

(54) DUAL CARDIAC CT SCANNER

(75) Inventors: Jiang Hsieh, Brookfield; Robert F. Senzig, Germantown, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/379,384

(22) Filed: Aug. 23, 1999

Related U.S. Application Data

(60) Provisional application No. 60/114,480, filed on Dec. 31, 1998.

(51) Int. Cl.[7] .............................................. G01N 23/00
(52) U.S. Cl. ............................................ 378/9; 378/19
(58) Field of Search .................. 378/9, 4, 19; 250/445

(56) References Cited

U.S. PATENT DOCUMENTS

| | | | |
|---|---|---|---|
| 4,991,190 A | * 2/1991 | Mori | 378/9 |
| 5,457,724 A | * 10/1995 | Toth | 378/4 |
| 5,469,487 A | * 11/1995 | Hu | 378/9 |

OTHER PUBLICATIONS

F. Rashid–Farrokhi, K.J.R. Liu, C.A. Bernestein, and D. Walnut, "Localized Wavelet Based Computerized Tomography," Proc. IEEE ICIP–95, pp. 445–448, 1995.

Carl Crawford and Kevin King, "Computed Tomography Scanning with Simultaneous Patient Translation," Med. Phys. 17(6), Nov./Dec. 1990, pp. 967–982.

* cited by examiner

Primary Examiner—Robert H. Kim
Assistant Examiner—Hoon K. Song
(74) Attorney, Agent, or Firm—Carl B. Horton, Esq.; Armstrong Teasdale LLP

(57) ABSTRACT

The present invention, in one form, is an imaging system for generating images of an entire heart. In one embodiment, projection data is collected for a field of view containing only the heart so that the total detector size is reduced. The smaller detector allows the use of a plurality of source-detector pairs so that projection data for an angular coverage of ($\pi$+fan angle) is collected by rotating a gantry significantly less than one complete rotation. Therefore, projection data is collected in significantly less than one cardiac cycle, minimizing motion artifacts.

30 Claims, 2 Drawing Sheets

DUAL CARDIAC CT SCANNER

CROSS REFERENCE TO RELATED APPLICATION

This application claims the benefit of U.S. Provisional Application No. 60/114,480, filed Dec. 31, 1998.

BACKGROUND OF THE INVENTION

This invention relates generally to computed tomography (CT) imaging and more particularly, to generating images of a heart.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In at least one known type of imaging system, commonly known as a computer tomography (CT) system, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. In addition to reduced scanning time, helical scanning provides other advantages such as improved image quality and better control of contrast.

In helical scanning, and as explained above, only one view of data is collected at each slice location. To reconstruct an image of a slice, the other view data for the slice is generated based on the data collected for other views. Helical reconstruction algorithms are known, and described, for example, in C. Crawford and K. King, "Computed Tomography Scanning with Simultaneous Patient Translation," Med. Phys. 17(6), November/December 1990.

In order to generate images of a rapidly moving object, such as a heart, known imaging systems have minimized motion artifacts, caused by the movement of the heart, by utilizing a high rotational speed gantry or by incorporating electron beam technology. However, the high speed gantry system significantly increases the force applied to the x-ray source and the detector affecting performance of the system. The electron beam technology requires a very complex design that significantly increases the cost of the scanner. As a result, few systems are capable of generating images of a moving heart without generating images containing significant motion artifacts.

To generate images of a heart, it is desirable to provide an imaging system which gathers data at a sufficiently high rate so that heart motion artifacts are minimized. It would also be desirable to provide such a system which generates such images of the entire heart using a single scan.

BRIEF SUMMARY OF THE INVENTION

These and other objects may be attained by a cardiac CT scanner that generates images of an entire object of interest using projection data collected from a plurality of detector arrays rotated less than a full rotation around the object. In accordance with one embodiment of the present invention, a plurality of angularly spaced source-detector array pairs are utilized to generate projection data of a limited area, or field of view, containing only the object of interest, so that motion artifacts are minimized. More specifically and in one embodiment, as a result of the quantity and spacing of the pairs, sufficient projection data is collected in less than one full rotation of the gantry to generate images of a heart. Particularly, sufficient projection data to generate an image of the entire heart is collected in significantly less than one cardiac cycle. As a result, motion artifacts are minimized in the reconstructed images.

In one embodiment, two source-detector pairs are utilized to generate images of the entire heart without significant motion artifacts. By collecting projection data for a limited field of view containing only the heart, the size of the detector array is reduced and minimized motion artifact images are generated by collecting $\pi$ plus a fan angle, which is the angle of the beam projected from the x-ray source, of projection data. More specifically, where the pairs are offset with respect to each other by an angle, $\beta$, equal to the quantity of $(\pi + \text{fan angle})/\text{the number of pairs}$, so that little overlapped data is collected, the images may be generated by rotating the gantry $(\pi + \text{fan angle})/\text{the number of pairs}$ degrees.

Particularly to generate images of the heart, initially the patient is positioned so that the patient's heart is centered at an iso-center of the system, for example by performing one or more scout scans. A scan is then completed by enabling x-ray sources of each of the source-detector pairs, and collecting projection data as the gantry is rotated. The projection data, collected during a period significantly less than a typical cardiac cycle, is then reconstructed. As a result of the timing of the data collection, motion artifacts are virtually eliminated from the reconstructed images of the heart.

In another embodiment, the size of the detector arrays of each source-detector array pair may be further reduced by generating images of the entire heart by performing at least two separate scan of the heart. For example, by performing two scans, the number of rows of each detector is reduced by one-half. The projection data from each scan are then combined to generate an image of the entire heart.

In another embodiment, each source-detector pair source has at least two focal spots. By properly selecting the spacing between the focal spots, images of the same heart volume are collected using a further reduced size detector.

The above described system generates images of the heart by gathering data at a sufficiently high rate so that heart motion artifacts are minimized. In addition, the system generates such images of the entire heart using a single scan.

DETAILED DESCRIPTION OF THE INVENTION

Figure 1:
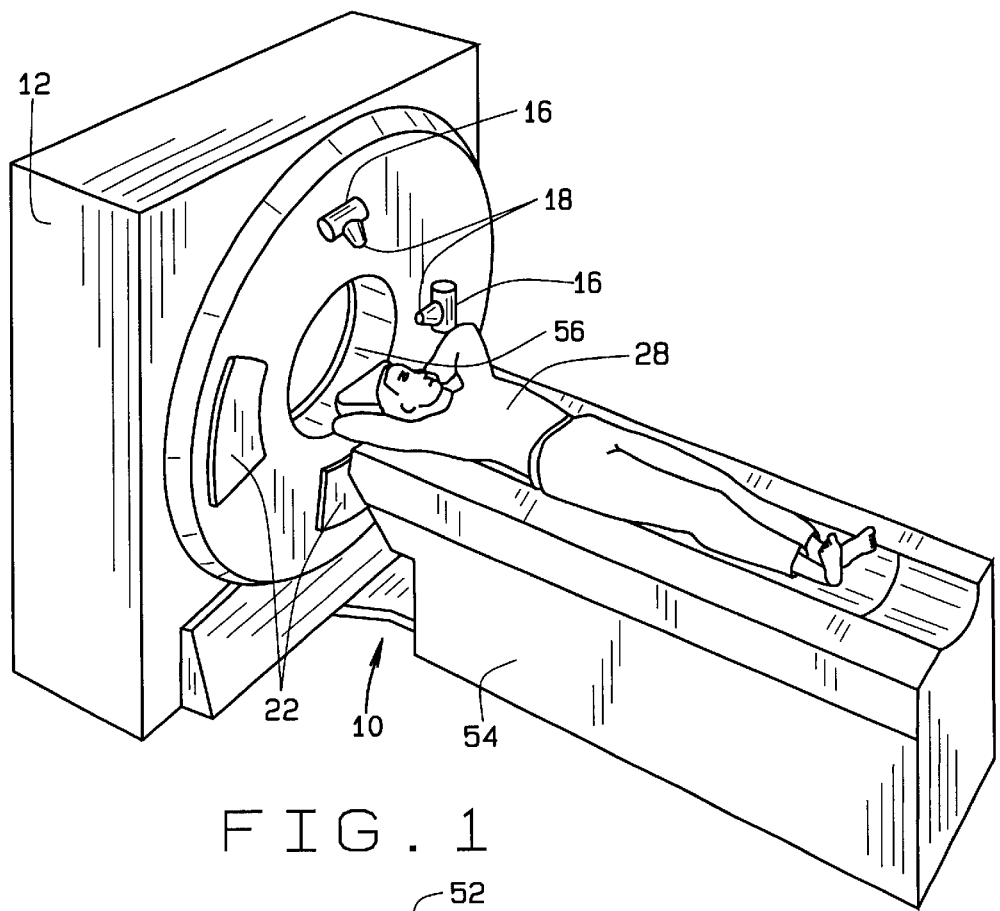
FIG. 1 is a pictorial view of a CT imaging system.
Figure 2:
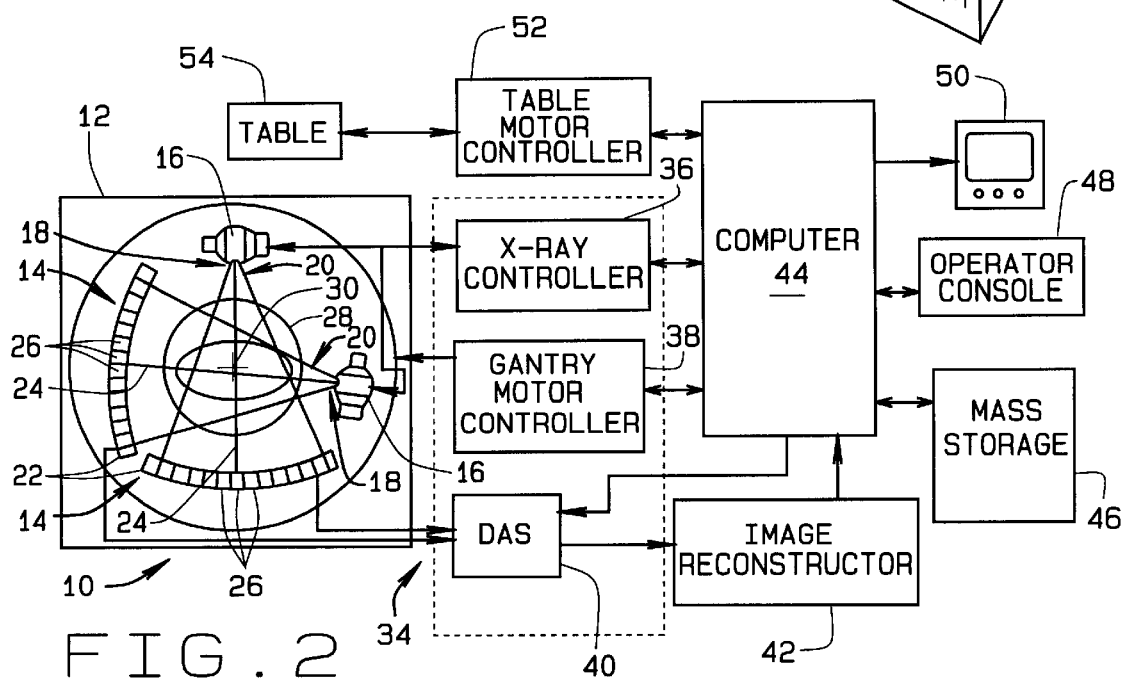
FIG. 2 is a block schematic diagram of the system illustrated in FIG. 1.

Referring to FIGS. 1 and 2, a computed tomograph (CT) imaging system 10 is shown as including a gantry 12 having a plurality of source-detector pairs 14. Each source-detector pair 14 includes an x-ray source 16 that projects from a focal spot 18 a beam of x-rays 20 toward a detector array 22 on the opposite side of gantry 12. X-ray beams 20 extend from x-ray source 16 along a beam plane 24. Beam plane 24, generally referred to as the "fan beam plane", contains the centerline of focal spot 18 and the centerline of beam 20 of each source-detector pair 14. Each x-ray beam 20 is collimated by a collimator (not shown) to lie within in an X-Y plane of a Cartesian coordinate system and generally referred to as an "imaging plane". Each detector array 22 is formed by an x-y array of detector elements 26 which together sense the projected x-rays that pass through a medical patient 28. Each detector array 22 may be a single slice detector or a multi-slice detector. Each detector element 26 produces an electrical signal that represents the intensity of an impinging x-ray beam and hence the attenuation of the beam as it passes through patient 28. During a scan to acquire x-ray projection data, gantry 12 and the components mounted thereon rotate about a center of rotation, or iso-center, 30.

More specifically and in one embodiment, each source-detector pair 14 is coupled to gantry 12 and angularly displaced about said gantry 12 so that an angle β exists between each beam plane 24. Particularly, the β angle between each source-detector pair 14 represents the angle, or angular rotation, between each beam plane 24. In one embodiment, the angle β is determined so that the little projection data overlap is collected as described below in more detail.

Rotation of gantry 12 and the operation of x-ray sources 16 are governed by a control mechanism 34 of CT system 10. Control mechanism 34 includes an x-ray controller 36 that provides power and timing signals to x-ray sources 16 and a gantry motor controller 38 that controls the rotational speed and position of gantry 12. A data acquisition system (DAS) 40 in control mechanism 34 samples analog data from detector elements 26 and converts the data to digital signals for subsequent processing. An image reconstructor 42 receives sampled and digitized x-ray data from DAS 40 and performs high-speed image reconstruction. The reconstructed image is applied as an input to a computer 44, which stores the image in a mass storage device 46.

Computer 44 also receives commands and scanning parameters from an operator via console 48 that has a keyboard. An associated cathode ray tube display 50 allows the operator to observe the reconstructed image and other data from computer 44. The operator supplied commands and parameters are used by computer 44 to provide control signals and information to DAS 40, x-ray controller 36 and gantry motor controller 38. In addition, computer 44 operates a table motor controller 52, which controls a motorized table 54 to position patient 28 in gantry 12. Particularly, table 54 moves portions of patient 28 through a gantry opening 56.

In one embodiment, in order to generate images of the entire heart of patient 28, projection data is collected for a limited area, or field of view, containing only the heart. By limiting the collection of projection data to the reduced field of view, the total detector size, e.g., the number of elements 26, is reduced. For example, where a typical human heart is scanned within a 15–20 cm field of view, the detector size in the x-y plane and the z-axis, or patient axis, can be significantly reduced from current CT scanner designs. More specifically, the size of the detector, as measured by the number of elements, N, is a function of the required radius of field of view, F, at iso-center 30, a source to iso-center distance, A, a source to detector distance, D, and the size of each detector element 26 along the fan angles direction in x-y plane, E. In one embodiment, the size, e.g., number of elements 26, of detector 22 is determined in accordance with:

$$N = \left(\frac{2*D}{E}\right)\sin^{-1}\left(\frac{F}{A}\right)$$

For example, in order to scan a field of view of 20 cm or 200 mm (radius=100 mm) with a system 10 having a source to iso-center distance of 630 mm, a source to detector distance of 1099.31 mm, and a detector element size of 1.0166 mm, the number of elements in the fan beam direction is $$N = \left(\frac{2*1099.31}{1.0166}\right)\sin^{-1}\left(\frac{100}{630}\right) \cong 344$$

requiring 344 elements 26 to provide projection data for the entire field of view. This is significantly smaller than at least one known CT scanner utilizing a detector having 852 elements. In one embodiment, the detector includes the same number of elements in the x-y plane and the z-axis so that images of the entire object of interest, e.g., heart, are generated.

Figure 3:
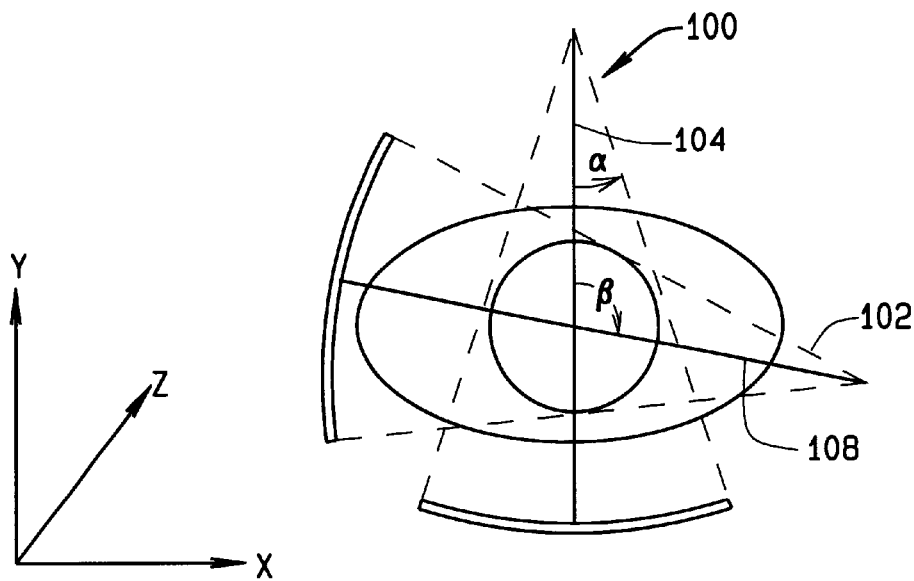
FIG. 3 is a pictorial view of two source-detector array pairs in accordance with one embodiment of the present invention.

As a result of the reduced detector size, the number of detector arrays 22 capable of being coupled to gantry 12 can be increased to reduce the amount of rotation required to generate images of the heart. More specifically and in one embodiment, system 10 includes a plurality of source-detector pairs 14. Utilizing source-detector pairs 14, images of the entire heart are generated by collecting (π plus a fan angle) of projection data. In one embodiment and as shown in FIG. 3, source-detector pairs 100 and 102 are utilized to generate images of the entire heart without significant motion artifacts. More specifically, first source-detector pair 100 has a beam plane 104 and second source-detector pair 102 has a beam plane 108. In order to reduce the amount of rotation of gantry 12 required to collect (π+fan angle), source-detector pairs 100 and 102 are angularly displaced about gantry 12 so that the amount of overlapped projection data collected is minimized. More particularly, source-detector pairs 100 and 102 are positioned so that first plane 104 and second plane 108 are offset with respect to each other by an angle β determined in accordance with:

$$\beta = \frac{(\pi + fan\ angle)}{number\ of\ source - detector\ array\ pairs}$$

For example, using the dimensions provided in the previous examples and using source-detector pairs 100 and 102, β is determined in accordance with ((180 degrees+18 degrees)/2), or 99 degrees.

In operation, images of the heart are generated by positioning patient 28 on table 54 and collecting projection data. More specifically and in one embodiment, patient 28 is positioned on table 54 so that the patient's heart is centered at iso-center 30, for example by performing one or more scout scans as known in the art. A scan is then completed by enabling x-ray sources 11 and collecting projection data using detector arrays 22 of source-detector pairs 100 and 102 as gantry 12 is rotated. More specifically, gantry 12 is rotated so that (π+fan angle) projection data is collected. For example, using the dimensions provided in the previous examples and where β equal (180+18)/2 or 99 degrees, rotating gantry 12 by 99 degrees, projection data for (π+fan angle), e.g., 198 degrees, is collected. Assuming a gantry speed of one rotation in 0.5 seconds, the projection data is collected in ((99/360)*0.5), or 0.138 seconds.

The collected projection data, representing a period significantly smaller than a typical cardiac cycle, is then reconstructed. Particularly and in one embodiment, the images of the entire heart are reconstructed using a wavelet based reconstruction algorithm, as known in the art, to avoid truncation artifacts associated with the limited field of view scan. As a result of the timing of the data collection, motion artifacts are virtually eliminated from the reconstructed images of the heart. In addition, using known methods, e.g., an EKG signal may be utilized to collect the projection data during known periods of reduced motion of the heart. To avoid artifacts due to the inconsistency of the boundary projections between two source-detector pairs, the amount of projection data could be slightly larger than β. The overlapped projections can then be combined using a weighting function for data from each source-detector pair, which is based upon the amount of overlap by each source-detector pair to produce the final image. In another embodiment, the size of each detector array 22 of each source-detector pair 14 may be further reduced by generating images of the entire heart from at least two separate scans of the heart. More specifically, the number of rows extending in the z-axis of each detector 22 may be reduced by the number of scans performed. For example, where two scans are performed, the number of rows of each detector 22 may be reduced by a factor of 2. After performing the scans, the collected the projection data is combined to generate an image of the entire heart.

Figure 4:
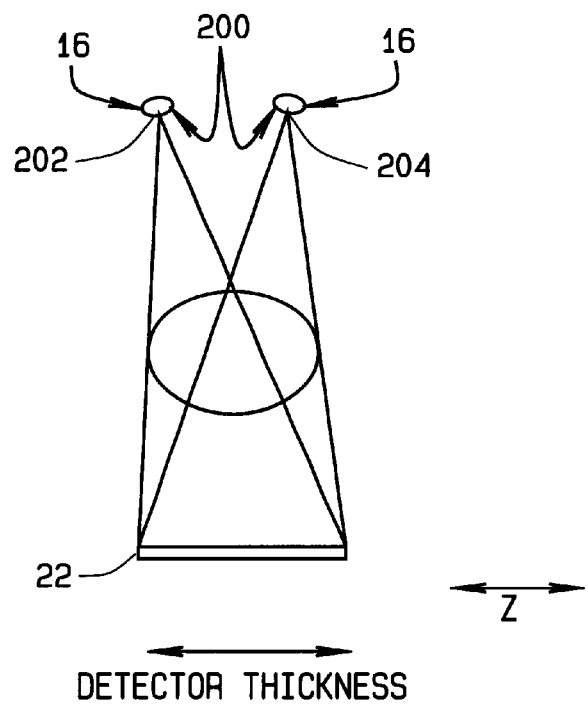
FIG. 4 is a pictorial view of a multiple focal spot source in accordance with one embodiment of the present invention.

In another embodiment and as shown in FIG. 4, each source-detector pair x-ray source 16 includes a plurality of focal spots 200, for example a first focal spot 202 and a second focal spot 204. By properly selecting the z-axis spacing between each focal spot 200, images of the same heart volume are collected using reduced size detectors 22. More specifically, by utilizing a plurality of focal spots 200, the z-axis dimension, or width of each detector 22 is reduced. Particularly, where a single focal spot x-ray source 16 is utilized, the width of each detector is α times the field of view at iso-center 30.

For example, for the dimensions of system 10 previously described, α =(1099.31/630) or 1.7. As shown in FIG. 4, using focal spots 202 and 204, α may be substantially reduced to approximately 1. As a result, the projection data for the same 20 cm field of view of the object, e.g., the heart, is collected using detector 22 having a z-axis width, or number of rows, of approximately (field of view at iso-center/detector element size). For example, (200/1.0166), or 197 rows.

The above described system generates images of the heart by gathering data at a sufficiently high rate by minimizing rotation of the gantry so that heart motion artifacts are minimized. In addition, the system generates such images of the entire heart using a single scan.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the present invention can be utilized in connection with single slice CT scanners, as well as many other CT systems including "fourth generation" systems. A "fourth generation" system is a system wherein the detector is a full-ring stationary detector and the x-ray source rotates with the gantry. In the fourth generation system, the outputs of each detector element are corrected to provide a uniform response. Accordingly, the spirit and scope of the invention are to be limited only by the terms of the appended claims.

What is claimed is:

1. An imaging system for generating an image of an object of interest, said system comprising:

a gantry;

a plurality of source-detector pairs, each said source-detector pair comprising a detector array and an x-ray source having at least one focal spot for emitting an x-ray beam along a scan plane toward said detector, each said source-detector pair angularly displaced about said gantry so that said projection data is collected for a defined field of view of the object of interest, said source-detector pairs are angularly displaced from each other by an angle β, wherein β is determined in accordance with:

$$\beta = \frac{(\pi + fan\ angle)}{number\ of\ source - detector\ array\ pairs}.$$

2. An imaging system in accordance with claim 1, wherein said system comprises two source-detector array pairs.

3. An imaging system in accordance with claim 2, wherein said fan angle is 18 degrees and said β is 99 degrees.

4. An imaging system in accordance with claim 1 wherein β is large enough to cause a portion of said projection data from one said source-detector pair, to overlap a portion of said projection data from a second said source-detector pair.

5. An imaging system in accordance with claim 6 wherein the overlapping portions of said projection data are combined using weighting functions based on an amount of overlap by each source-detector pair.

6. An imaging system for generating an image of an object of interest, said system comprising:

a gantry;

a plurality of source-detector pairs, each said source-detector pair comprising a detector array and an x-ray source having at least one focal spot for emitting an x-ray beam along a scan plane toward said detector, each said source-detector pair angularly displaced about said gantry so that said projection data is collected for a defined field of view of the object of interest, a number of elements of each said detector array in x-y plane are determined in accordance with:

$$N = \left(\frac{2*D}{E}\right)\sin^{-1}\left(\frac{F}{A}\right)$$

where:
 F is the defined radius of field of view at a system iso-center,
 A is a source to iso-center distance,
 D is a source to detector distance, and
 E is a size of each detector element in x-y plane.

7. A system in accordance with claim 1 wherein each said x-ray source includes a plurality of focal spots displaced in the z-axis.

8. A system in accordance with claim 1 wherein said source-detector pairs are rotatable about said gantry.

9. A system in accordance with claim 1 wherein said field of view comprises a heart of the object of interest.

10. A system in accordance with claim 9 wherein said projection data is collected in less than one cardiac cycle of the heart.

11. An imaging system in accordance with claim 1 wherein said x-ray source and said detector array are coupled to said gantry.

12. An imaging system in accordance with claim 1 wherein said x-ray source is coupled to said gantry and said detector arrays are portions of a full-ring stationary detector.

13. A method of generating an image using a computed tomography system, the system including a plurality of source-detector pairs, each pair including a detector array and an x-ray source emitting x-ray beams toward the detector array, said method comprising:
 identifying an object of interest of the object;
 collecting projection data of the identified object for an angular range of (π+fan angle) using the source-detector pairs, wherein the source-detector pairs are angularly displaced from each other by an angle β, wherein β is determined in accordance with:

$$\beta = \frac{(\pi + fan\ angle)}{number\ of\ source - detector\ array\ pairs}; \text{ and}$$

reconstructing the collected projection data.

14. A method in accordance with claim 13 wherein each x-ray source includes at least one focal spot, and wherein collecting projection data of the identified object comprises the steps of:
 emitting x-ray beams from each source focal spot toward each detector array; and
 collecting projection data using each detector array.

15. A method in accordance with claim 14 wherein the system includes two source-detector array pairs and wherein emitting x-ray beams from each source focal spot toward each detector array comprises the steps of:
 using a first source-detector pair to emit a first x-ray beam along a first beam plane toward a first detector array; and
 using a second source-detector pair to emit a second x-ray beam along a second beam plane toward a second detector array.

16. A method in accordance with claim 13, wherein the fan angle is 18 degrees and β is 99 degrees.

17. A method in accordance with claim 13, wherein β is large enough to cause a portion of said projection data from one said source-detector pair, to overlap a portion of said projection data from a second said source-detector pair.

18. A method in accordance with claim 17 further comprising the step of:
 combining the overlapping portions of said projection data using weighting functions based on an amount of overlap by each source-detector pair.

19. A method in accordance with claim 13, wherein collecting projection data of the identified object for an angular range of (π+fan angle) using the source-detector pairs comprises the step of rotating the source-detector pairs, about the gantry, at least β degrees.

20. A method in accordance with claim 13 wherein identifying an object of interest of the object comprises the step of defining a field of view.

21. A method in accordance with claim 20 further comprising the step of positioning a center of the object of interest at an iso-center of the system.

22. A method in accordance with claim 20 wherein positioning a center of the object of interest at an iso-center of the system comprises the step of performing at least one scout scan.

23. A method in accordance with claim 20, wherein a number of elements in x-y plane of each said detector array is determined in accordance with:

$$N = \left(\frac{2*D}{E}\right)\sin^{-1}\left(\frac{F}{A}\right)$$

where:
 F is the defined radius of field of view at the system iso-center,
 A is a source to iso-center distance,
 D is a source to detector distance, and
 E is a size of each detector element in x-y plane.

24. A method in accordance with claim 13 wherein each x-ray source includes a plurality of focal spots.

25. A system in accordance with claim 6 wherein each said x-ray source includes a plurality of focal spots displaced in the z-axis.

26. A system in accordance with claim 6 wherein said source-detector pairs are rotatable about said gantry.

27. A system in accordance with claim 6 wherein said field of view comprises a heart of the object of interest.

28. A system in accordance with claim 27 wherein said projection data is collected in less than one cardiac cycle of the heart.

29. An imaging system in accordance with claim 6 wherein said x-ray source and said detector array are coupled to said gantry.

30. An imaging system in accordance with claim 6 wherein said x-ray source is coupled to said gantry and said detector arrays are portions of a full-ring stationary detector.

* * * * *

UNITED STATES PATENT AND TRADEMARK OFFICE
CERTIFICATE OF CORRECTION

PATENT NO.    : 6,421,412 B1
DATED         : July 16, 2002
INVENTOR(S)   : Jiang Hsieh et al.

It is certified that error appears in the above-identified patent and that said Letters Patent is hereby corrected as shown below:

<u>Column 6,</u>
Line 38, delete "6" insert therefor -- 4 --.

Signed and Sealed this

Thirteenth Day of January, 2004

JON W. DUDAS
*Acting Director of the United States Patent and Trademark Office*